United States Patent [19]

Cushman

[11] 4,321,472
[45] Mar. 23, 1982

[54] PANORAMIC DENTAL X-RAY MACHINE WITH CAMERA DETACHED THEREFROM

[75] Inventor: Robert H. Cushman, Princeton, N.J.

[73] Assignee: Pennwalt Corporation, Philadelphia, Pa.

[21] Appl. No.: 142,481

[22] Filed: Apr. 21, 1980

[51] Int. Cl.³ .................. G01N 23/00; G21K 5/06; G11B 1/00
[52] U.S. Cl. .................. 250/439 P; 250/446; 250/468
[58] Field of Search .................. 250/439 P, 490, 446, 250/469, 468

[56] References Cited

U.S. PATENT DOCUMENTS

| | | | |
|---|---|---|---|
| 2,684,446 | 7/1954 | Paatero | 250/323 |
| 3,445,655 | 5/1969 | Curry | 250/469 |
| 3,617,742 | 11/1971 | Schulman et al. | 250/490 |
| 3,737,660 | 6/1973 | Ando et al. | 250/439 P |
| 3,743,832 | 7/1973 | Wright | 250/320 |
| 3,792,281 | 2/1974 | Schwartz et al. | 250/439 P |
| 4,147,662 | 4/1979 | Schwartz | 250/439 P |
| 4,221,970 | 9/1980 | Ciavattoni | 250/439 P |

Primary Examiner—Alfred E. Smith
Assistant Examiner—Carolyn E. Fields
Attorney, Agent, or Firm—Arthur M. Suga

[57] ABSTRACT

Panoramic dental X-ray machine wherein the camera assembly is physically detached from the tubehead assembly to prevent their rotation as an integral unit around the patient's head. Essentially, the detached camera assembly, modified in accordance with one aspect of the invention, is positioned above the head of the patient and its semi-cylindrical film carrier carries X-ray film therewith. The film carrier is cupped about the patient's face with an inner drum or mask configured similarly to the film carrier interposed between the film carrier and patient's face. The film carrier and film are then rotated at slow non-linear speeds by the film drive mechanism of the camera assembly in accordance with the type radiograph desired, i.e., continuous or discontinuous. The many advantages of the disclosed panoramic X-ray machine are cited.

1 Claim, 8 Drawing Figures

PANORAMIC DENTAL X-RAY MACHINE WITH CAMERA DETACHED THEREFROM

STATEMENT OF THE INVENTION

This invention relates to a panoramic dental x-ray machine wherein the camera assembly is physically detached from the tubehead assembly, and consequently, the assemblies are not rotatable as a unit.

BACKGROUND AND SUMMARY OF THE INVENTION

Known prior art panoramic dental X-ray machines are characterized by an arm rigidly interconnecting the tubehead and camera assemblies. The tubehead-camera assembly thus rotates as a unit around the head of the patient being radiographed. The patient is seated in the patient chair and positioned therein by means of a bite block slidably adjustably supported on a rod mounted in cantilever fashion, thus permitting undesirable head and jaw movement relative to the camera assembly notwithstanding the fact that the patient's chin is resting on a suitable chin rest assembly. The tubehead-camera assembly is then positioned to be in approximate visual alignment with some distinguishing feature of the patient's face. It is recognized that it is a most difficult task to accurately align the patient's head by conventional bite blocks, chin rests, and the like, since a dental arch varies in size and shape from person to person and bears no significant relationship to chin and head structure. Even when the same patient is radiographed on different occasions, adjustment and alignment are difficult to repeat.

It is noted that the distance from patient to film is much less than the distance from the patient to the tubehead. In a present model panoramic dental x-ray machine of the assignee, shown in FIG. 1 of the drawings, the distance between the film plane to teeth incisal edge is approximately 2.6" whereas the distance from the focal spot of the X-ray tube in the tubehead to teeth incisal edge is approximately 14.5". It is apparent that the patient to film distance is more critical and more sensitive to minor inaccuracies which can cause noticeable variations in the resultant image.

In the present invention, patient to film alignment and distance is fixed. Thus precise alignment of the tubehead to camera is less critical. It is appreciated that even though the camera assembly and tubehead assembly rotate as a unit in prior art machines, the camera is still vertically adjustable and must be aligned with the tubehead and patient. The patient's head, in the present invention, may be directly visually aligned with the film and camera.

The camera assembly, including the inner substantially semi-cylindrical drum or mask, are separated from the tubehead assembly and consequently do not rotate about the patient's head. The film is attached to and wrapped around a semi-cylindrical film carrier, although the invention is not limited to such configuration, and the film carrier caused to rotate at controlled non-uniform speeds in accordance with the type of radiograph desired. The film is thus limitedly rotated around the patient's face about a vertical axis parallel to the center line of the patient's face. A light-opaque but X-ray transmitting mask is interposed between the camera and patient, the mask rigidly supporting a bite block which is substantially inflexible.

The advantages of the present invention are many and varied. For example:

(a) Radiographing of the same or different patients are characterized by more repeatable positioning of both equipment and patients to provide more reliable radiographs resulting in improved diagnostic evaluations.

(b) Since the distance between the tubehead and camera may be varied, a more uniform and controlled magnification can be provided, not attainable with a fixed spacing therebetween.

(c) Human error is minimized as necessary manual adjustments by the operator are made easier.

(d) Weight of the rotating tubehead and camera assembly is markedly reduced. The sturdiness required in the structure illustrated in FIG. 1 of the drawings is necessitated by the horizontal cantilevered arm holding the camera. The entire "C" arm of this prior art structure can be eliminated and the tubehead mounted on a less massive pedestal or column to thus minimize mechanical complexity and clutter, as well as lowering cost, reducing vibrations, and facilitating radiographing in either direction of rotation of the tubehead assembly.

(e) Speed of rotation of the tubehead can be independently regulated to provide a wider focal trough at the centrals or incisors.

(f) The patient is not aware of camera rotation or movement about his face which may be psychologically more comforting.

These and other advantages will become more apparent as the invention is further described in conjunction with the drawings wherein.

DETAILED DESCRIPTION OF THE INVENTION

Figure 1:
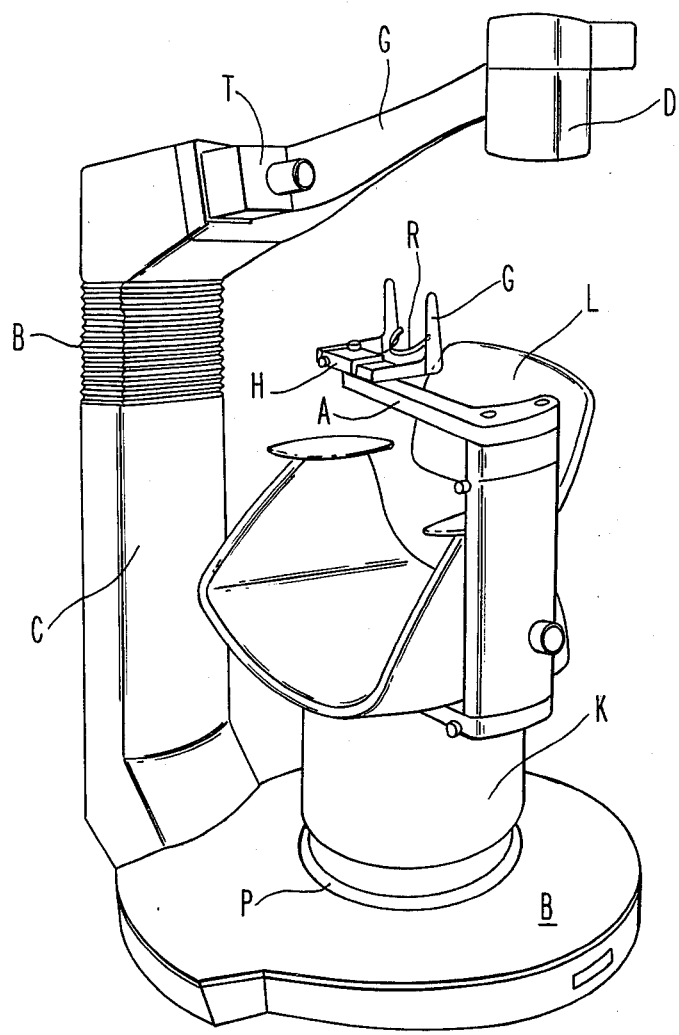
FIG. 1 is a perspective view of a prior art panoramic dental X-ray machine of the present assignee.

Referring to FIG. 1 of the drawings, panoramic dental x-ray machine comprises a base B having a stationary platform P disposed generally centrally thereof. Platform P supports a patient chair L including an adjustable chin-rest R for supporting the chin of the patient, with the patient'head being held between a pair of spaced upright adjustable guides G. The chinrest R and guides G are carried by a housing H adjustably supported on an arm A of chair L. The arm may be raised or lowered by conventional means. Knobs for its adjustment or positioning are illustrated in the drawing. Column C is caused to rotate around chair L, the column carrying a tubehead T, a camera supporting arm G, and a camera assembly D which houses mechanism for driving the X-ray film therein at non-linear speeds in accordance with the type radiograph desired, i.e., continuous or discontinuous. Bellows B permit vertical adjustment of tubehead T on column C. The film drive mechanism, per se, is described and claimed in copending patent applications of Ciavattoni et al., Ser. No. 25,127, filed Mar. 29, 1979, now U.S. Pat. No. 4,247,779, for "Link-Clutch Film Drive Mechanism For Panoramic Dental X-Ray Machine"; and Ser. No. 49,242, filed June 18, 1979, now U.S. Pat. No. 4,221,970, for "Panoramic Dental X-Ray Machine Employing Selectable Mode Film Drive Mechanism With Shiftable Cam Followers", both allowed, and both patent applications incorporated herein by reference.

The chair and mechanism for its shift or transport is located below chair L, within shroud K, the shift or transport mechanism being bolted to stationary platform P. Other mechanism for causing column C to rotate around stationary platform P is supported and partially housed in base B and is described and claimed in U.S. Pat. No. 4,168,633, incorporated by reference herein. Mechanism for causing the chair to travel in a controlled X-Y plane in accordance with the type radiograph desired is described in U.S. Pat. No. 4,125,774, also incorporated by reference herein, and further described in allowed patent application Ser. No. 2,148, filed Jan. 9, 1979, for "Panoramic Dental X-Ray Machine X-Motion Drive", now abandoned in favor of a continuation-in-part application, Ser. No. 25,706, now U.S. Pat. No. 4,251,730, of Cushman et al., filed Apr. 2, 1979, same title, both incorporated by reference herein.

Figure 2:
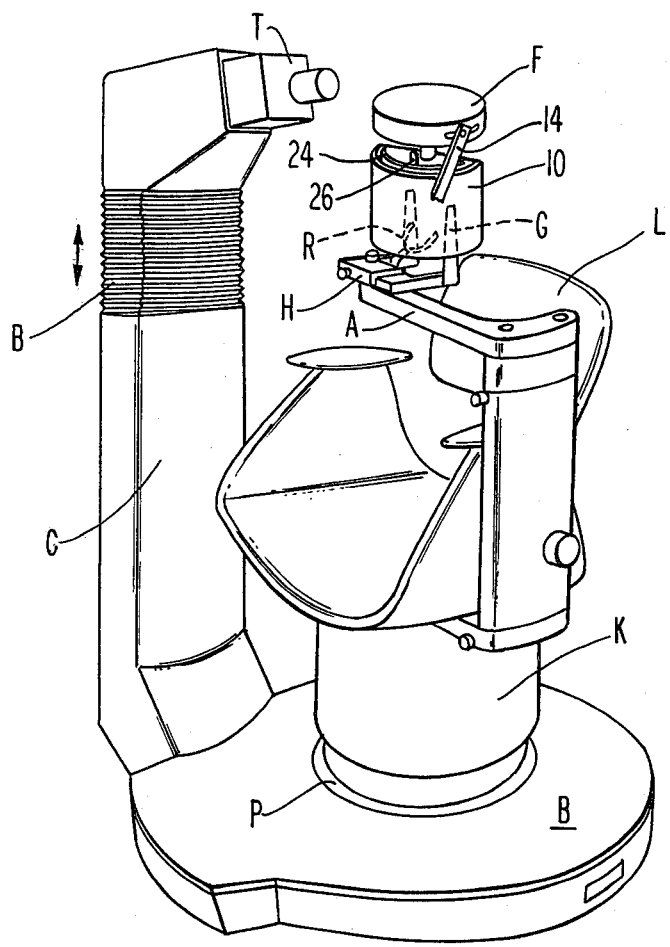
FIG. 2 is a view similar to FIG. 1 with the camera assembly detached from the tubehead assembly and modified in accordance with one aspect of the invention.
Figure 3:
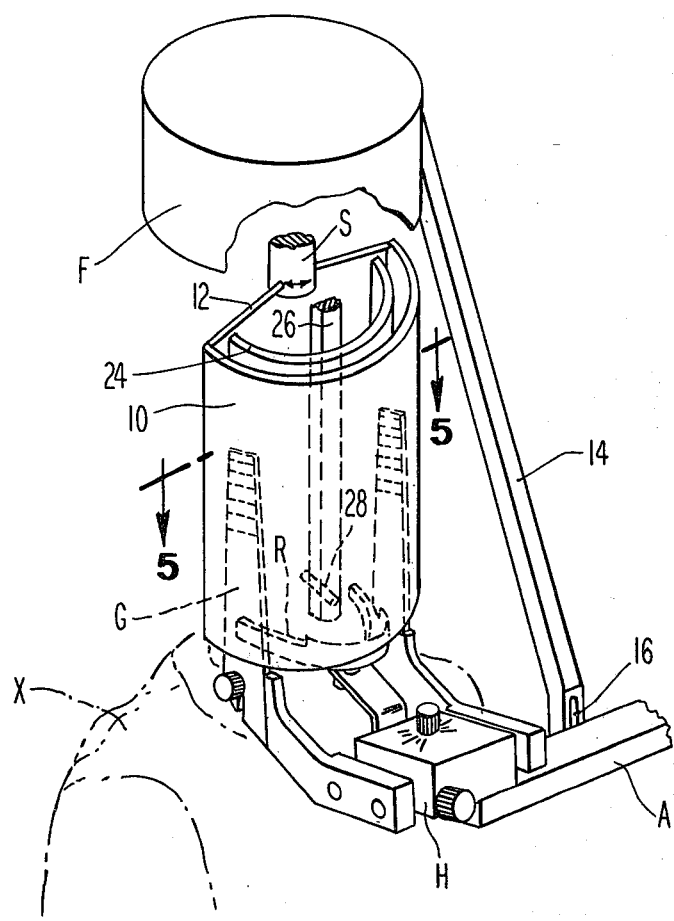
FIG. 3 is a perspective view of the detached and modified camera assembly of FIG. 2 operably positioned about a seated patient.
Figure 4:
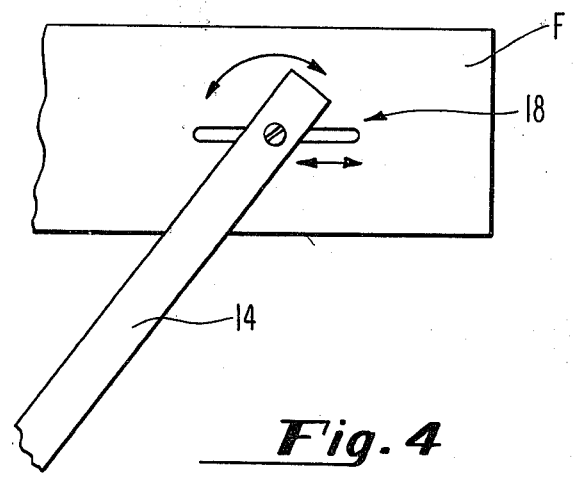
FIG. 4 is a side elevational view of a portion of the means for adjusting the positioning of the camera assembly.

Referring to FIG. 2, camera supporting arm G is eliminated resulting in the separation or detachment of camera assembly D from the integral rotating unit of the tubehead-camera assembly. Camera assembly D is modified as clearly shown in FIG. 3. The film drive mechanism referred to hereinabove is enclosed within housing F. Output shaft S of the film drive mechanism rotates at a non-linear speed and, unlike the cylindrical drums shown and described in the patent applications above-mentioned, film carrier 10 is illustrated semi-cylindrical and rotates with shaft S by means of spokes 12. The entire film drive mechanism may be supported by a bracket member 14 (FIG. 4), interconnecting arm A and film drive housing F. Height of the film drive mechanism may be controlled by means of slotted adjustment 16 while its horizontal positioning and angular displacement are effected through pin and slot means 18.

Figure 5:
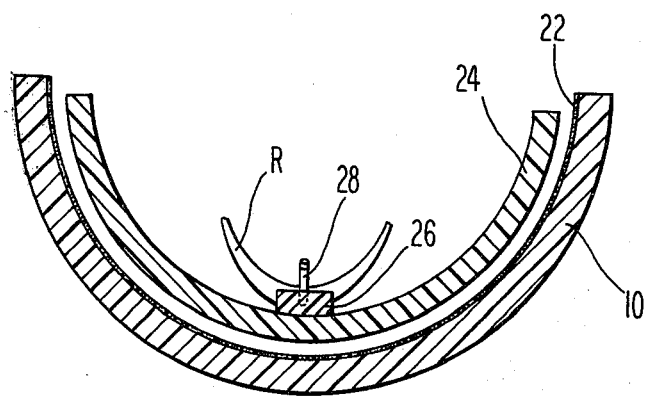
FIG. 5 is a sectional view of FIG. 3 taken along line 5—5 thereof, parts omitted for clarity.

Film carrier 10 may be semi-elliptical or arcuately configured as desired. Film carrier 10 should be capable of permitting X-rays generated within tubehead T to pass readily therethrough and suitably may comprise a rigid pre-formed acrylic type plastic, carbon filled material or even wood. X-ray film 22 is ordinarily wrapped around the inner surface of film carrier 10 (FIG. 5) but may be wrapped around the outer surface thereof. Film carrier 10 rotates with shaft S about the head of patient X.

An inner semi-cylindrical drum or mask 24 is disposed interiorly of film carrier 10 in spaced relationship thereto and will be similarly configured. Mask 24 is preferably a carbon filament composite plastic material of extreme stiffness which is X-ray transparent and light-opaque. It is conveniently supported from film drive housing F, removable therefrom and adjustable thereon, by means of rod 26, preferably of the same material as mask 24, and must similarly be X-ray transmitting. Mask 24 will normally be pre-formed to its arcuate configuration and may be alternatively supported by channel members at its upper and lower edges, or at its vertical edges, and the like, and, of course, does not rotate with film carrier. Since mask 24 is light-opaque, patient X is substantially unaware of the slowly rotating film carrier 10 and film 22. A bite block 28 is rigidly supported on rod 26 and is readily removable therefrom and adjustable thereon by known means.

In the operation of the present panoramic dental X-ray machine, patient X is seated in chair L and properly positioned therein by means of chin-rest R and bit block 28. The tubehead and camera and film drive mechanism are aligned. Radiographing of the patient is initiated by means of a single switch (not shown) which starts rotation of tubehead T on column C with shaft S of the film drive mechanism.

Figure 6:
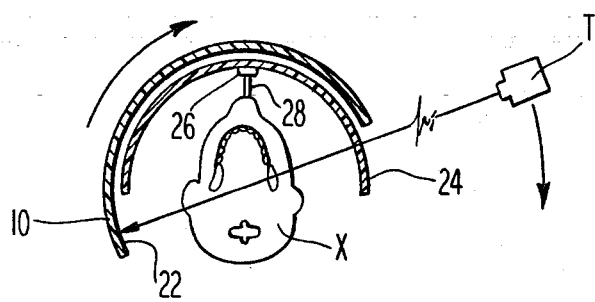
FIGS. 6, 7 and 8 are diagrammatic representations depicting progressive steps in radiographing a patient's dental arch-temporolmandibular joint area.
Figure 7:
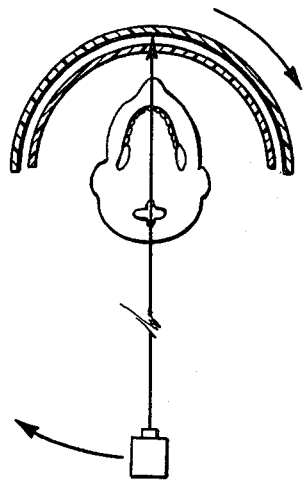
Figure 8:
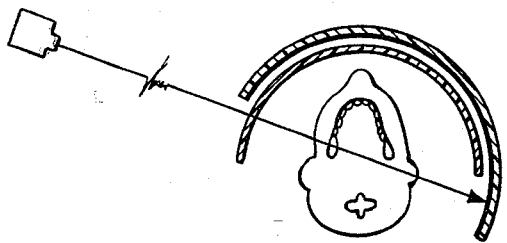

By coordinating the movement of chair L with the mode selected for driving the film at non-linear speeds, the patient is radiographed in a continuous or discontinuous mode. More specifically and referring to FIg. 6 of the drawings, X-rays from tubehead T pass under the right temporomandibular joint area of patient X and strike film 22 positioned interiorly of film carrier 10. As tubehead T rotates, the left temporomandibular joint is radiographed. The X-rays are readily transmitted through mask 24. As tubehead T further rotates about the patient as illustrated in FIG. 7, film carrier 10 is similarly rotating, but completely physically independently of tubehead T, and the patient's centrals are radiographed. In FIG. 8, the right temporomandibular joint area has just been radiographed and the x-rays are now shown under the left temporomandibular joint. It is apparent from FIGS. 6 through 8, that at no time is film 22 double exposed during the radiographing of patient P. Further, the film is only required to travel a short distance. More specifically, in the prior art cameras, a slot is disposed centrally thereof and the film is moved sequentially past the slot starting from one end of the film to other. Thus, the linear length of the camera is necessarily approximately twice the length of the film. In the present invention, the film is approximately prepositioned for imaging each area of the dental arch-temporomandibular joint area. Hence, the film only needs to travel at appropriate speeds for considerably shorter distances in order to provide the proper tomographic blurring. It is appreciated that the speed of rotation of shaft S may readily be varied as described in the film drive mechanism patent applications hereinabove referred to. Further referring to FIGS. 6-8, and to FIG. 3, mask 24 may be physically engaged by ear plugs (not shown), transparent to X-rays, of course, extending from the patient's ears, to further stabilize alignment between patient and film.

The present invention contemplates the possibility of the film remaining stationary within the camera assembly, i.e, not driven by the film drive mechanism. Thus, slit radiography would be practiced rather than tomography. Additionally a camera slit, the only purpose of which is to reduce scatter, may be employed with the disclosed structure. If so used, its movement may readily be coordinated with that of tubehead T.

It is appreciated that the X-ray film may readily be positioned closer to or farther from the patient's face than in conventional or prior art equipment to thus modify the distance the film needs to travel in order to bring the desired plane in focus, all well known tomographic principles. The film may be positioned very close to the patient's face, requiring a minimum, or even possibly no movement or travel of the film. Clearly, the spacing of the film to the dental arch may be advantageously varied at different points along the arch.

Further, the film may be driven directly by means of a rotatable flexible shaft coupled to the output of a cam member driven by the rotating tubehead mechanism.

It is appreciated that the present invention may be practiced on a standing patient, in addition to the patient being seated, by suitably mounting the camera to a stationary platform such as base B.

I claim:

1. In a panoramic dental X-ray machine for providing continuous and discontinuous type radiographic images of dental arch-temporomandibular joint area of a patient seated in a chair mounted for movement in accordance with type image desired, the improvement to said machine comprising a column extending upwardly from said machine for carrying a tubehead containing an X-ray source for generating X-rays, means for powering said X-ray source, said column rotating about said seated patient, a camera assembly having film for activation by said X-rays, said camera assembly being detached from said tubehead and mounted on said chair in alignment with said tubehead for receiving said X-rays after passing through said dental arch, said camera assembly being adjustably mounted to said patient chair and with respect to said patient, means for maintaining said camera assembly in said receiving alignment with said tubehead while said tubehead rotates about said patient, means for non-linearly driving said film in said camera assembly in accordance with type radiographic image desired, said camera assembly including an output shaft driven by said means for non-linearly driving said film, drum means rotating in accordance with said output shaft, said film mounted to said drum means whereby non-linear rotation of said shaft causes said drum means and said film to rotate in accordance therewith, said drum means including a substantially semi-cylindrical drum cupped about the face of said patient, said drum rotating on a substantially vertical axis such that rotation of said drum about said axis causes said drum to continually pass in close proximity to said patient's face, said chair being provided with head positioning means, an X-ray transmitting mask configured for stationary disposition in spaced relationship between said drum and patient's face, said mask being adjustably supported on a rod interconnecting said means for non-linearly driving said film in said camera assembly and said mask, said mask being light-opaque, and a bite block rigidly extending from said rod.

* * * * *